US00PP10981P

United States Patent [19]

Sorensen

[11] Patent Number: Plant 10,981

[45] Date of Patent: Jun. 29, 1999

[54] OSTEOSPERMUM PLANT NAMED 'DURBAN'

[75] Inventor: Carl Aksel Kragh Sorensen, Aabyhoj, Denmark

[73] Assignee: Paul Ecke Ranch, Encinitas, Calif.

[21] Appl. No.: 08/959,900

[22] Filed: Oct. 29, 1997

[51] Int. Cl.[6] ..... A01H 5/00

[52] U.S. Cl. ..... Plt./360

[58] Field of Search ..... Plt./68.1, 360

*Primary Examiner*—Howard J. Locker

*Assistant Examiner*—Melissa L. Kimball

*Attorney, Agent, or Firm*—C. A. Whealy

[57] ABSTRACT

A distinct cultivar of Osteospermum plant named 'Durban', characterized by its rounded and upright growth with dense foliage and erect flower stems; moderate growth rate; white ray florets with violet blue disc florets; and numerous inflorescences per plant.

3 Drawing Sheets

The present invention relates to a new and distinct cultivar of Osteospermum plant, botanically known as *Osteospermum ecklonis* and referred to by the cultivar name Durban. The new Osteospermum is marketed under the name Cape Daisy Durban.

The new cultivar is a product of a planned breeding program conducted by the inventor in Abyhoj, Denmark. The objective of the breeding program was to create new Osteospermum cultivars having uniform plant habit, interesting floret colors, and large and numerous inflorescences.

The new cultivar originated from a cross made by the inventor of the nonpatented *Osteospermum ecklonis* cultivar Cape Daisy Lubuto as the female, or seed, parent with an unidentified *Osteospermum ecklonis* proprietary selection of the inventor as the male, or pollen, parent. The new Osteospermum was selected from the progeny of this cross in a controlled environment in Abyhoj, Denmark.

Asexual reproduction of the new cultivar by terminal cuttings taken at Abyhoj, Denmark, has shown that the unique features of this new Osteospermum are stable and reproduced true to type in successive generations.

The following traits have been repeatedly observed and are determined to be the unique characteristics of 'Durban'. These characteristics in combination distinguish 'Durban' as a new and distinct cultivar:

1. Upright, rounded and relatively compact growth habit with dense foliage and erect flower stems.
2. Moderate growth rate.
3. White ray florets with violet blue disc florets.
4. Numerous inflorescences per plant. Plants flower continuously.

The cultivar Durban has not been obeserved under all possible environmental conditions. The phenotype may vary somewhat with variations in environment such as temperature, daylength and light intensity, without, however, any variance in genotype.

Plants of the new Osteospermum can be compared to plants of the female parent, the nonpatented cultivar Cape Daisy Lubuto. However, in side-by-side comparisons conducted in Abyhoj, Denmark, plants of the new Osteospermum differed in ray floret color and had more ray florets per inflorescence than plants of the cultivar Cape Daisy Lubuto.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph on the first sheet comprises a side perspective view of a typical flowering plant of 'Durban'.

The photogragh on the second sheet is a close-up view of typical inflorescences of 'Durban'.

The photograph on the third sheet comprises a comparison side perspective view of typical plants of the female parent, the cultivar Cape Daisy Lubuto, (left) and the cultivar Durban (right). Foliage and floret colors in the photographs may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown outdoors in containers during the spring in Encinitas, Calif. and Keller, Tex. Measurements and numerical values represent averages for typical flowering plants.

Botanical classification: *Osteospermum ecklonis* cultivar Durban.

Parentage:

*Female, or seed, parent.*—*Osteospermum ecklonis* cultivar Cape Daisy Lubuto (not patented).

*Male, or pollen, parent.*—Unidentified *Osteospermum ecklonis* proprietary selection of the inventor.

Propagation:

*Type.*—Terminal tip cuttings.

*Time to initiate roots.*—Summer: About 10 days at 18° C. Winter: About 12 days at 18° C.

*Time to develop roots* (*time required to produce a rooted cutting*).—Summer: About 28 days at 18° C. Winter: About 35 days at 18° C.

*Rooting habit.*—Fine, fibrous and somewhat branched.

Plant description:

*Appearance.*—Perennial herbaceous container and garden plant. Rounded, upright and relatively compact. Dense foliage and erect flower stems. Freely branching and growth rate is moderate.

*Plant height.*—About 33 cm.

*Foliage description.*—Leaves alternate, single. Length, fully expanded leaves: About 8.5 cm. Width, fully expanded leaves: About 3 cm. Shape: Oblanceolate. Apex: Cuspidate. Base: Attenuate, leaves sessile. Margin: Widely-spaced teeth, 3 to 4 per edge. Aspect: Flat. Texture: Very fine pubescence on both surfaces and at margins. Fragrance: Strongly fragrant, typical of species. Color: Young foliage, upper surface: 147A. Young foliage, under surface: 147B. Fully expanded foliage, upper surface: 147A. Fully expanded foliage, under surface: 147B. Attenuated leaf base: 146D. Venation, upper surface: 146B. Venation, under surface: 146C.

Inflorescence description:

*Appearance.*—Daisy-type composite inflorescence form. Inflorescences borne on terminals above foliage, arising from leaf axils. Disc and ray florets arranged acropetally on a capitulum. One inflorescence per flowering stem. Inflorescences persistent.

*Flowering response.*—Under natural conditions, plants flower continuously from April to Octover in the Northern Hemisphere.

*Fragrance.*—Not detectable.

*Inflorescence size.*—Diameter: About 6.5 cm. Depth (height): About 1.5 cm. Diameter of disc: About 1.2 cm.

*Opening inflorescences.*—Length: About 1.3 cm. Width: About 1 cm. Shape: pointed. Color: 144A.

*Ray florets.*—Length: About 3cm. Width: About 8 mm. Shape: Oblanceolate. Apex: Rounded or sometimes emarginate with 3 lobes. Margin: Entire. Texture: Satiny, smooth. Number of ray florets per inflorescence: About 24. Color: When opening: 4A. Mature, upper surface: 155B/155D with purple, 77B, at base. Mature, under surface: 10A with greenish blue stripes.

*Disc florets.*—Length: About 7 mm. Width: About 1 mm at base, flaring to about 3 mm at apex. Shape: Tubular, slightly funnel-shaped. Number of disc florets per inflorescence: Numerous. Color: Immature: 94A. Mature: Close to 89A.

*Peduncle.*—Length: About 15 cm. Diameter: About 1.5 mm. Aspect: Wiry, inflorescences held erect above foliage. Texture: Rough, slightly pubescent. Color: 144A.

*Sepals.*—Appressed to ray florets. Shape: Narrowly lanceolate with pointed apex. Quantity: About 20 per inflorescence. Texture: Rough with short coarse hairs. Color: 144A.

*Reproductive organs.*—Androecium: Present on disc florets only. Anthers: One per disc floret, 5-parted. Pollen: Golden to orange-yellow, moderate. Gynoecium: Present on ray and disc florets. Stigma: Bipartite. Style: Purple. Ovary: Inferior, green in color.

Disease resistance: No known Osteospermum diseases observed to date on plants grown under commercial production conditions.

Seed production: Seed production has not been observed.

It is claimed:

1. A new and distinct cultivar of Osteospermum plant named 'Durban', as illustrated and described.

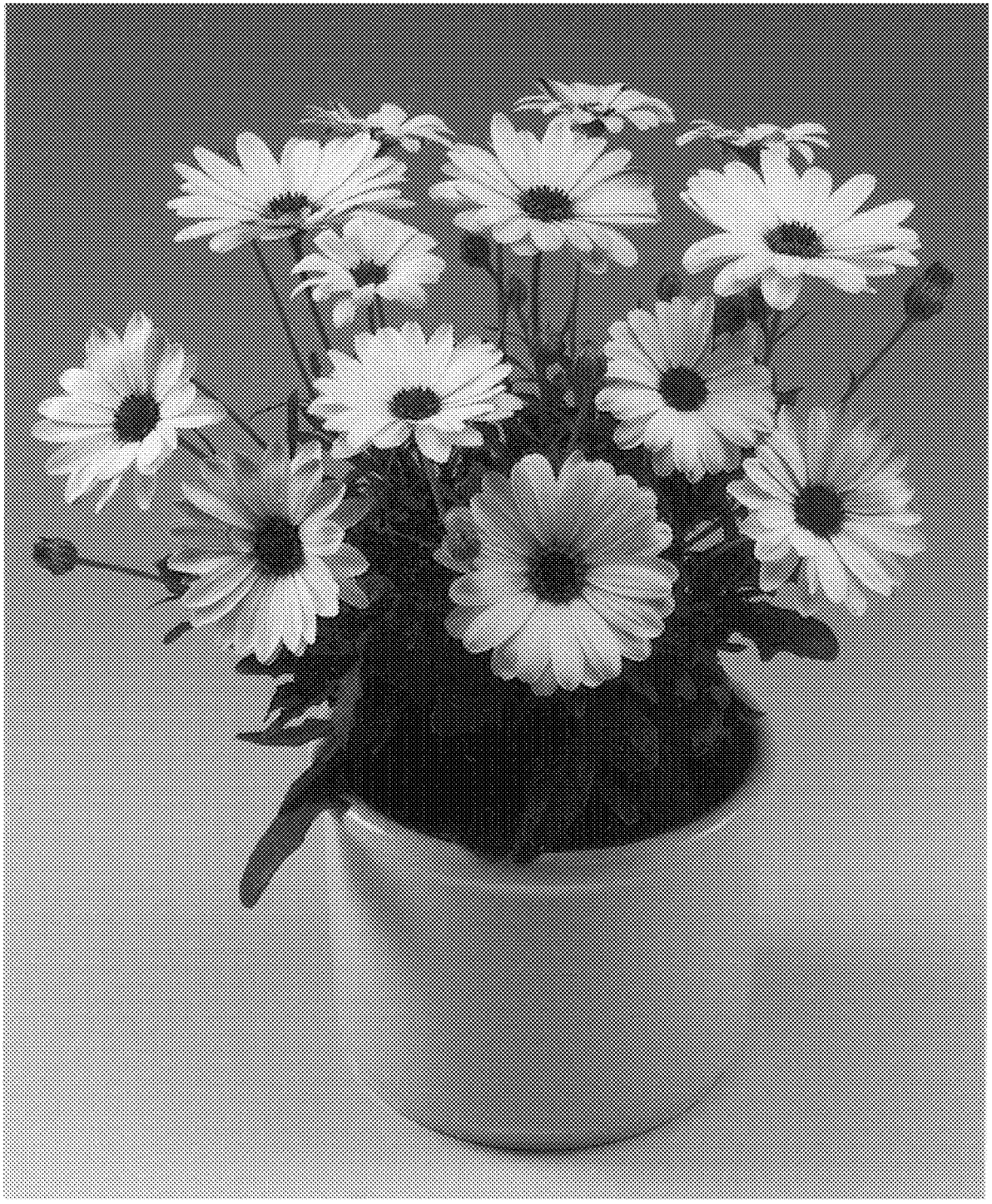

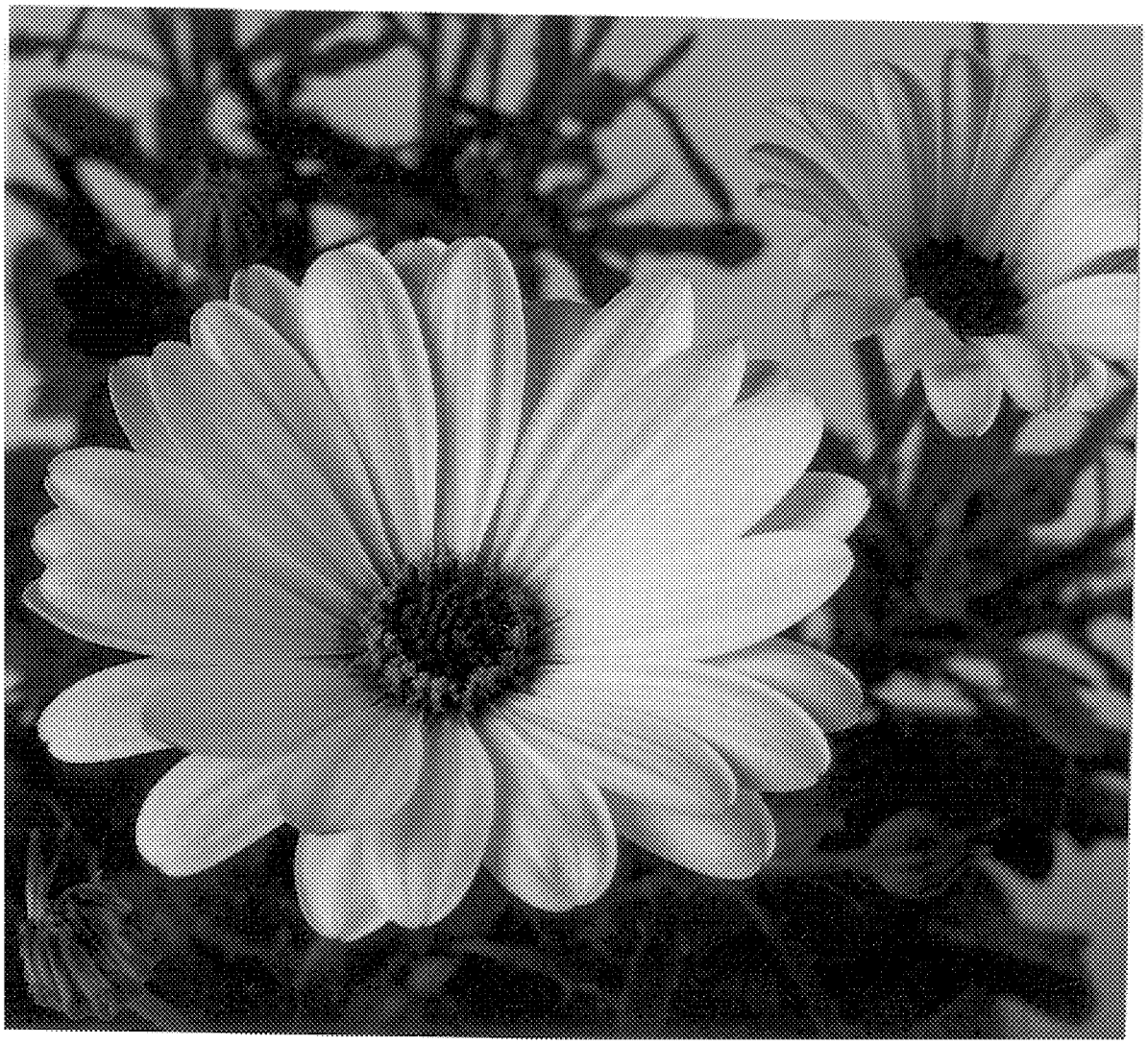

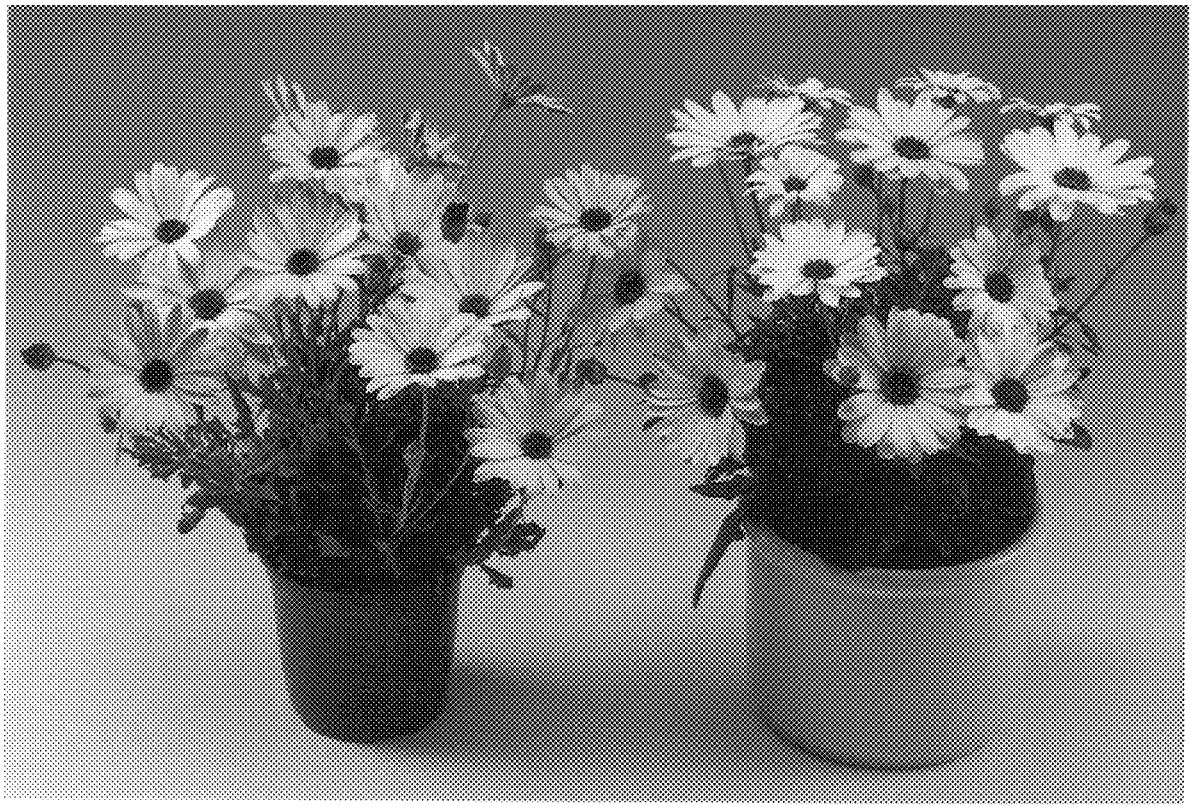

* * * * *